United States Patent
Ma et al.

(10) Patent No.: US 11,517,722 B2
(45) Date of Patent: Dec. 6, 2022

(54) CONFIRMATION OF CATHETER PLACEMENT WITHIN A VEIN

(71) Applicant: Becton, Dickinson and Company, Franklin Lakes, NJ (US)

(72) Inventors: Yiping Ma, Layton, UT (US); S. Ray Isaacson, Layton, UT (US); Weston F. Harding, Lehi, UT (US); Joseph Spataro, Cottonwood Heights, UT (US); Huy Tran, Riverton, UT (US); Jonathan Karl Burkholz, Salt Lake City, UT (US); Mohankumar Natesan, Singapore (SG); Kiat Jin Cheng, Singapore (SG); Kathryn Willybiro, Park City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 366 days.

(21) Appl. No.: 16/741,911

(22) Filed: Jan. 14, 2020

(65) Prior Publication Data

US 2020/0230369 A1 Jul. 23, 2020

Related U.S. Application Data

(60) Provisional application No. 62/794,439, filed on Jan. 18, 2019.

(51) Int. Cl.
*A61M 25/06* (2006.01)
*A61M 25/00* (2006.01)
*A61M 25/01* (2006.01)

(52) U.S. Cl.
CPC .... *A61M 25/0693* (2013.01); *A61M 25/0015* (2013.01); *A61M 25/0067* (2013.01);
(Continued)

(58) Field of Classification Search
CPC .............. A61M 25/0693; A61M 25/06; A61M 25/0606; A61M 25/065; A61M 25/0015;
(Continued)

(56) References Cited

U.S. PATENT DOCUMENTS 4,180,068 A   12/1979 Hansen et al.
4,317,445 A * 3/1982 Robinson .......... A61M 25/0693
                                                       D24/112
(Continued)

FOREIGN PATENT DOCUMENTS

JP    2000262628    9/2000
WO    2009/049823   4/2009
WO    2018/219842   12/2018

*Primary Examiner* — James D Ponton
(74) *Attorney, Agent, or Firm* — Kirton McConkie; Whitney Blair; Kevin Stinger

(57) ABSTRACT

A catheter system may include a catheter adapter, which may include a distal end and a proximal end. The catheter system may include a catheter, which may include a distal end, a proximal end, a catheter lumen extending through the distal end of the catheter and the proximal end of the catheter, and an inner surface forming the catheter lumen. The catheter may extend distally from the distal end of the catheter adapter. The distal end of the catheter may include one or more holes. The distal end of the catheter may include one or more channels. The holes and/or the channels may facilitate visualization of blood flashback indicating the catheter is disposed within a vein of a patient.

8 Claims, 15 Drawing Sheets

(52) U.S. Cl.
CPC ............... *A61M 2025/0002* (2013.01); *A61M 2025/0166* (2013.01)

(58) Field of Classification Search
CPC ...... A61M 25/0067; A61M 2025/0002; A61M 2025/0166
See application file for complete search history.

(56) References Cited

U.S. PATENT DOCUMENTS

| | | | |
|---|---|---|---|
| 5,279,572 A * | 1/1994 | Hokama | A61M 25/0693 604/168.01 |
| 5,911,705 A | 6/1999 | Howell | |
| 2004/0122415 A1 | 6/2004 | Johnson | |
| 2007/0255220 A1 * | 11/2007 | King | A61M 5/32 604/168.01 |
| 2008/0103483 A1 * | 5/2008 | Johnson | A61M 25/008 604/524 |
| 2014/0171770 A1 * | 6/2014 | Hann | A61B 5/05 604/510 |
| 2014/0180066 A1 | 6/2014 | Stigall | |
| 2015/0038908 A1 | 2/2015 | Antonucci | |
| 2015/0367103 A1 | 12/2015 | Pajunk et al. | |
| 2016/0331938 A1 | 11/2016 | Blanchard et al. | |
| 2018/0093074 A1 | 4/2018 | Burkholz et al. | |
| 2019/0054270 A1 * | 2/2019 | Bornhoft | A61M 25/0606 |
| 2019/0307989 A1 | 10/2019 | Ma et al. | |

\* cited by examiner

CONFIRMATION OF CATHETER PLACEMENT WITHIN A VEIN

RELATED APPLICATIONS

This application claims the benefit of U.S. Provisional Patent Application No. 62/794,439, filed Jan. 18, 2019 and entitled CONFIRMATION OF CATHETER PLACEMENT WITHIN A VEIN, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are generally inserted at a shallow angle through the skin into vein of the patient.

In order to verify proper placement of the introducer needle and/or the PIVC in the blood vessel, a clinician generally confirms that there is blood "flashback." In further detail, in some instances, the introducer needle may include a notch. In response to the sharp distal tip of the introducer needle being positioned within vasculature of the patient, blood may flow proximally through a lumen of the introducer needle and exit the needle lumen through the notch.

The blood may then travel proximally between an outer surface of the introducer needle and an inner surface of the PIVC, which may be transparent. Thus, the clinician may visualize the blood and thereby confirm placement of the introducer needle within the vasculature. Once placement of the needle has been confirmed, the clinician may temporarily occlude flow in the vein and remove the introducer needle, leaving the PIVC in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, a catheter system may include a catheter adapter, which may include a distal end, a proximal end, and a catheter adapter lumen extending through the distal end of the catheter adapter and the proximal end of the catheter adapter. In some embodiments, the catheter system may include a catheter, which may include a distal end, a proximal end, a catheter lumen extending through the distal end of the catheter and the proximal end of the catheter, and an inner surface forming the catheter lumen. In some embodiments, the catheter may extend distally from the distal end of the catheter adapter.

In some embodiments, the catheter system may include an introducer needle, which may extend through the catheter. In some embodiments, the introducer needle may include a sharp distal tip, which may be disposed distal to the distal end of the catheter. In some embodiments, the distal end of the catheter may include a distal opening, and the introducer needle may extend through the distal opening.

In some embodiments, the distal end of the catheter adapter may include one or more holes. In some embodiments, the catheter system may include a gap disposed between an outer surface of the introducer needle and an inner surface of the catheter. In some embodiments, the gap may be disposed within the catheter lumen. In some embodiments, the gap may be in fluid communication with the holes such that in response to the holes being inserted into a vein, blood may flow through the holes and into the gap. In some embodiments, all or a portion of the catheter may be transparent, and the gap may include a visualization channel in which blood flows and is visible to a clinician.

In some embodiments, the gap may be proximate the holes. In some embodiments, the gap may be annular. In some embodiments, the introducer needle may include one or more grooves. In some embodiments, a distal end of each of the grooves may be proximate a particular hole. In some embodiments, the gap may be disposed within the groove. In some embodiments, the holes may be arranged such that some of the holes are distal to other of the holes.

In some embodiments, the introducer needle may include a distal end, a proximal end, and an introducer needle lumen extending through the distal end of the introducer needle and the proximal end of the introducer needle, and an inner surface forming the introducer needle lumen. In some embodiments, the catheter system may include one or more sensors. In some embodiments, the sensors may be embedded in the inner surface of the introducer needle at the distal end of the introducer needle. Additionally, or alternatively, in some embodiments, the sensors may be embedded in the inner surface of the catheter at the distal end and proximate the gap.

In some embodiments, the sensors may be configured to detect the distal end of the introducer needle and/or the distal end of the catheter is within the vein. In some embodiments, the sensors may include bio-impedance sensors, pressure sensors, capacitance sensors, infrared sensors, or another suitable type of sensor. In some embodiments, a pattern or arrangement of the sensors may vary. In some embodiments, the sensors may be aligned with a bevel of the distal end of the introducer needle.

In some embodiments, a particular sensor may include a bio-impedance sensor, which may include a first electrode and a second electrode. In some embodiments, the first electrode may be embedded in the inner surface of the introducer needle at the distal end of the introducer needle or embedded in the in the inner surface of the catheter at the distal end and proximate the gap. In some embodiments, the second electrode may be configured to be secured to skin of a patient.

In some embodiments, the inner surface of the catheter may include one or more channels, which may extend from the distal opening. In some embodiments, the channels are configured to allow blood to flow between the outer surface of the introducer needle and the inner surface of the catheter in response to the distal end of the catheter being inserted into the vein.

In some embodiments, the introducer needle may include a notch. In some embodiments, the outer surface of the introducer needle may include a channel distal to the notch.

In some embodiments, a distal end of the channel may be disposed distal to the distal opening. In some embodiments, a proximal end of the channel may be proximate the gap. In some embodiments, the gap may be in fluid communication with the channel such that in response to the distal end of the channel being inserted into the vein, blood may flow through the channel and into the gap. In some embodiments, the notch may be proximate the gap.

In some embodiments, the gap may be in fluid communication with the channel and the notch. In some embodiments, the gap may be a first gap, and the catheter system may include a second gap disposed between an outer surface of the introducer needle and the inner surface of the catheter. In some embodiments, the second gap may be disposed within the catheter lumen. In some embodiments, the second gap may be in fluid communication with the notch such that in response to the introducer needle being inserted into the vein, the blood may flow into the introducer needle and out the notch into the second gap. In some embodiments, the first gap may be separated from the second gap.

In some embodiments, an absorbent material may be disposed within the notch and/or may extend proximally within the gap. In some embodiments, the absorbent material may be porous. In some embodiments, the absorbent material may be disposed within the introducer needle lumen and proximal to the notch. In some embodiments, in response to blood contacting the absorbent material, the absorbent material may expand and cover the notch.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
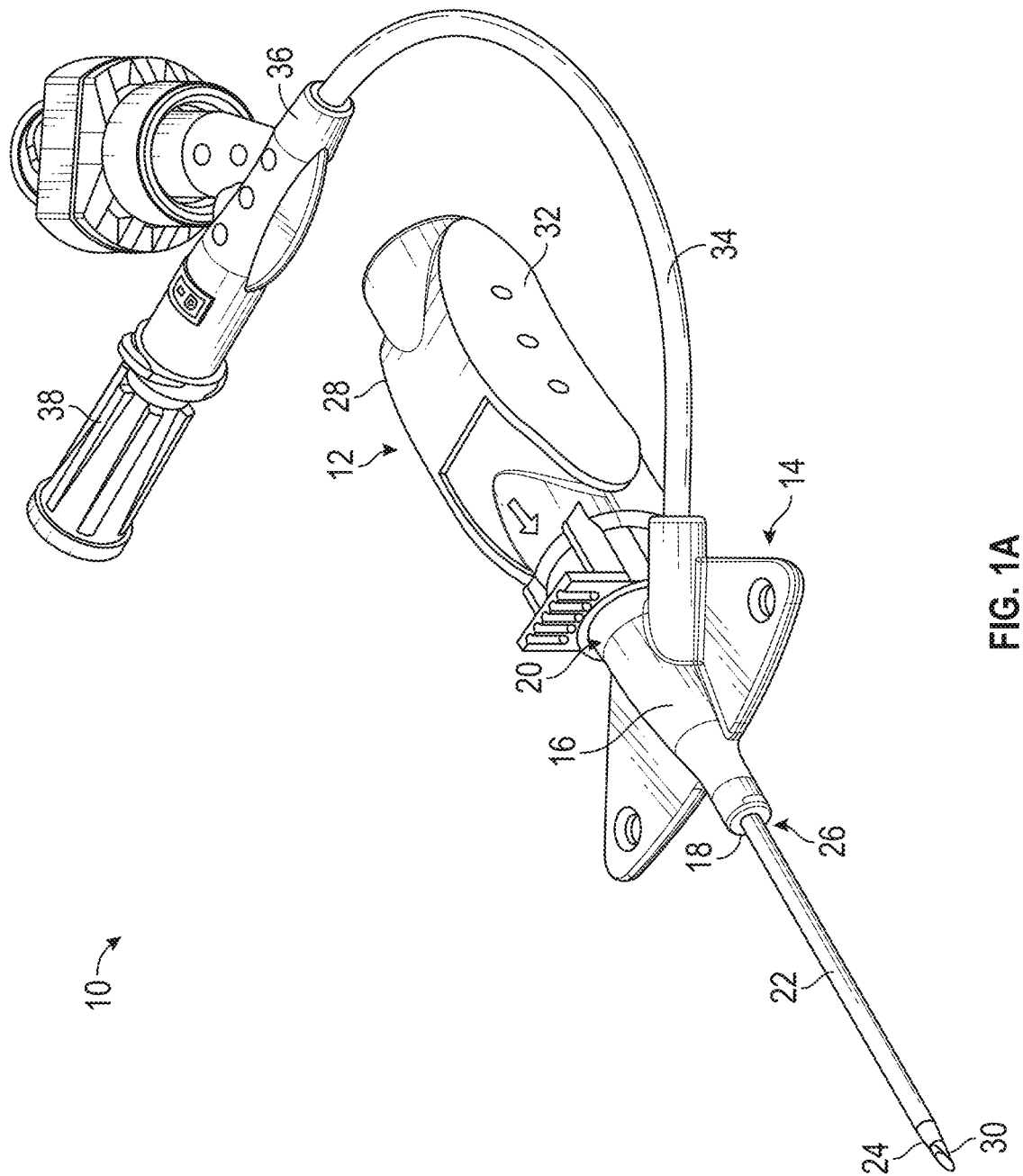
FIG. 1A is an upper perspective view of an example catheter system, according to some embodiments.
Figure 1B:
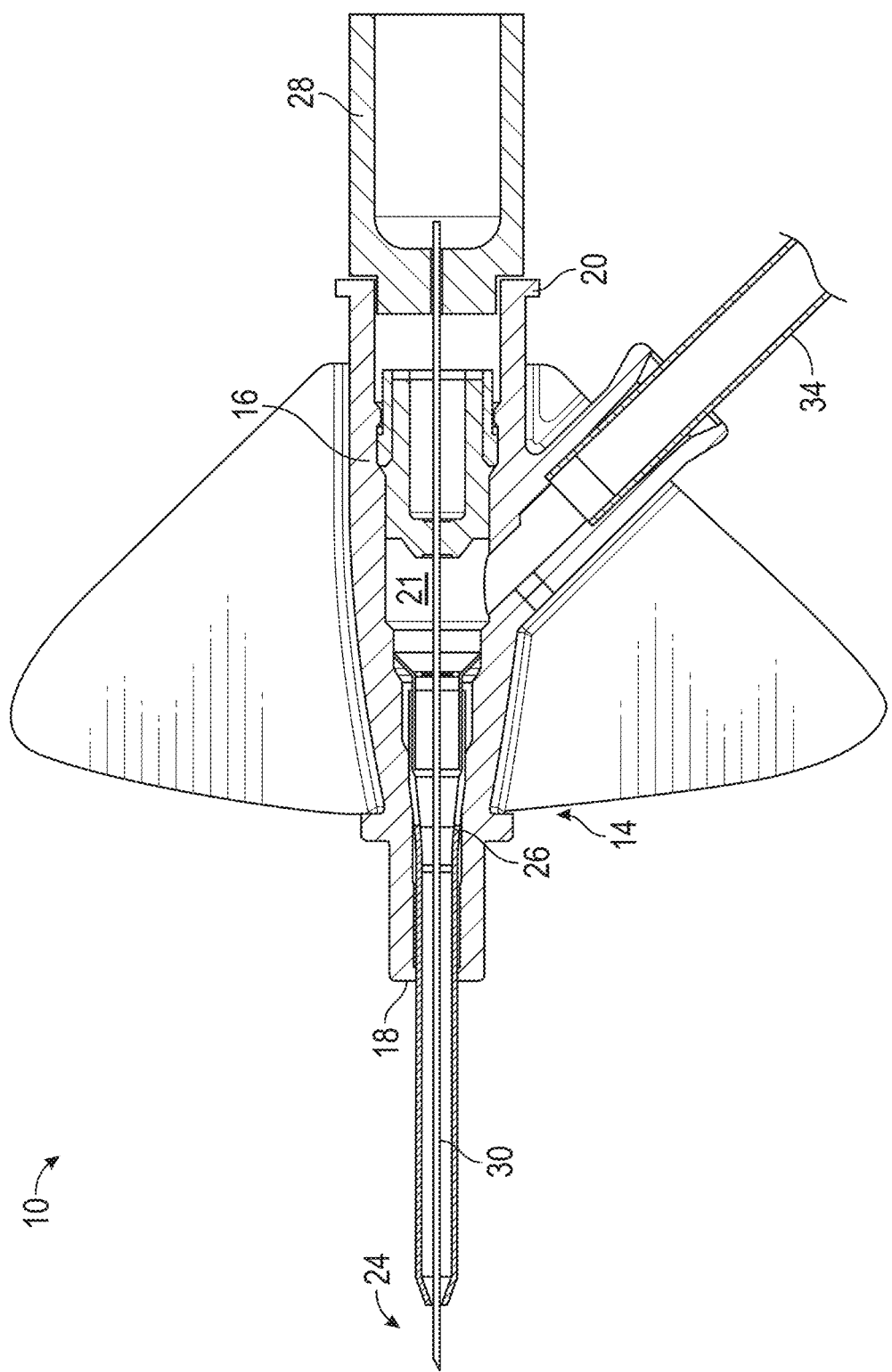
FIG. 1B is a cross-sectional view of the catheter system of FIG. 1A, according to some embodiments.

Referring now to FIGS. 1A-1B, in some embodiments, a catheter system 10 may include a needle assembly 12 and a catheter assembly 14. FIGS. 1A-1B illustrate the catheter system in an insertion position, ready for insertion into a vein of a patient, according to some embodiments. In some embodiments, the catheter assembly 14 may include a catheter adapter 16, which may include a distal end 18, a proximal end 20, and a catheter assembly lumen 21 extending through the distal end 18 and the proximal end 20. In some embodiments, the catheter assembly 14 may include a catheter 22, which may include a distal end 24 and a proximal end 26. In some embodiments, the catheter 22 may include a peripheral intravenous catheter ("PIVC"). In some embodiments, the proximal end 26 of the catheter 22 may be secured within the catheter adapter 16.

In some embodiments, the needle assembly 12 may include a needle hub 28, which may be removably coupled to the catheter adapter 16. In some embodiments, the needle assembly 12 may include an introducer needle 30. In some embodiments, a proximal end of the introducer needle 30 may be secured within the needle hub 28. In some embodiments, the introducer needle 30 may extend through the catheter 22 when the catheter system 10 is in an insertion position ready for insertion into the vein of a patient, as illustrated, for example, in FIGS. 1A-1B.

In some embodiments, the needle assembly 12 may include a needle grip 32, which a clinician may grip and move proximally to withdraw the introducer needle 30 from the vein once placement of the catheter 22 within the vein is confirmed. In some embodiments, the catheter system 10 may include an extension tube 34. In some embodiments, a distal end of the extension tube 34 may be coupled the catheter adapter 16 and a proximal end of the extension tube 34 may be coupled to an adapter 36.

In some embodiments, a fluid infusion device may be coupled to the adapter 36 to deliver fluid to the patient via the catheter 22 inserted in the vein, once the introducer needle 30 is removed from the catheter system 10. In some embodiments, a blood collection device may be coupled to the adapter 36 to withdraw blood from the patient via the catheter 22 inserted in the vein.

In some embodiments, the catheter system 10 may be integrated, having the extension tube 34 integrated within the catheter adapter 16, such as, for example, the BD NEXIVA™ Closed IV Catheter System, the BD NEXIVA™ DIFFUSICS™ Closed IV Catheter System, the BD PEGASUS™ Safety Closed IV Catheter System, or another integrated catheter system. An example of an integrated catheter system 10 is illustrated in FIGS. 1A-1B. In some embodiments, the catheter system 10 may be non-integrated, without the extension tube 34.

In some embodiments, the catheter system 10 may be vented to observe blood and facilitate proximal flow of blood within the introducer needle 30 and/or the catheter 22. In some embodiments, the catheter system 10 may be vented in any suitable manner. For example, a vent plug 38 may be coupled to the adapter 36 during insertion of the catheter assembly 14 into the patient. In some embodiments, the vent plug 38 may be permeable to air but not to blood. In some embodiments, the catheter 22, the catheter adapter 16, the extension tube 34, the adapter 36, and the vent plug 38 may be in fluid communication. As another example, in some embodiments, the needle hub 28 may include a flash chamber, an example of which is described in U.S. patent application Ser. No. 15/946,593, filed Apr. 5, 2018, entitled "INTRODUCER NEEDLE WITH NOTCHES FOR IMPROVED FLASHBACK," which is hereby incorporated by reference in its entirety.

Figure 2A:
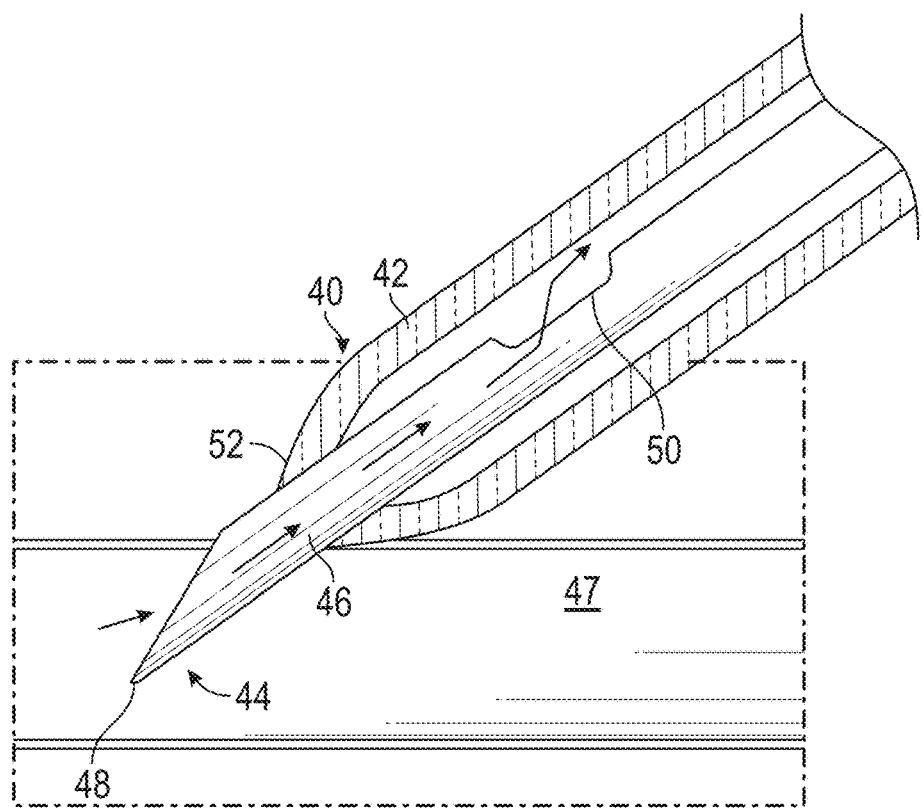
FIG. 2A is a cross-sectional view of a prior art catheter and a prior art introducer needle, disposed in an insertion position, according to some embodiments.

Referring now to FIG. 2A, a distal end 40 of a prior art catheter 42 and a distal end 44 of a prior art introducer needle 46 are illustrated. In response to the prior art introducer needle 46 being inserted into a vein 47 of the patient, blood may flow through a sharp distal tip 48 of the prior art introducer needle 46 and out a notch 50 in the prior art introducer needle 46 directly into an annular gap disposed between an outer surface of the prior art introducer needle 46 and an inner surface of the prior art catheter 42. The prior art catheter 42 may be transparent, which may allow the clinician to visualize the blood and confirm that the sharp distal tip 48 of the prior art introducer needle 46 is positioned within the vein 47 of the patient.

After confirming the sharp distal tip 48 is positioned within the vein 47 of the patient, the clinician is then typically instructed to lower an insertion angle and advance the prior art catheter 42 a short distance to ensure the distal end 40 of the prior art catheter 42 is in the vein 47 before threading the prior art catheter 42 off the prior art introducer needle 46. A distal tip 52 of the prior art catheter 42 is separated from a proximal end of a bevel of the distal end 44 of the prior art introducer needle 46 by a distance called "lie distance." Because a length of the bevel varies by gauge size of the prior art introducer needle 46, a distance the prior art catheter 42 needs to travel from when the sharp distal tip 48 penetrates the vein 47 to when the distal tip 52 of the prior art catheter 42 enters the vein 47 varies by gauge and lie distance. Many prior art catheter 42 insertions fail due to early threading of the prior art catheter 42 off the prior art introducer needle 46.

Figure 2B:
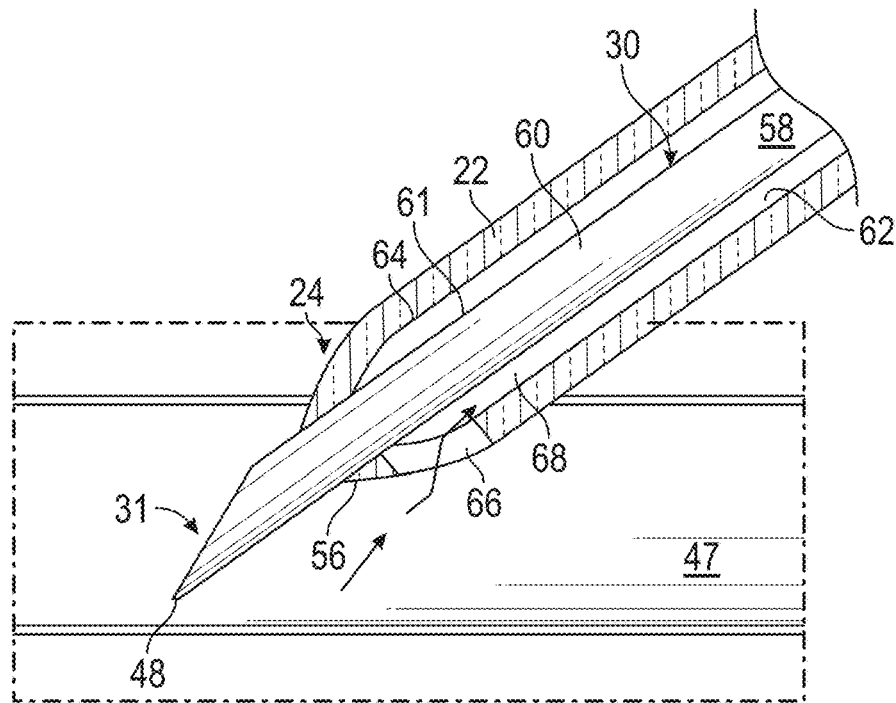
FIG. 2B is a cross-sectional view of an example catheter and an example introducer needle, disposed in the insertion position and which may be used with the catheter system of FIG. 1A, according to some embodiments.

Referring now to FIG. 2B, the distal end 24 of the catheter 22 and a distal end 31 of the introducer needle 30 are illustrated in the insertion position, according to some embodiments. In some embodiments, the introducer needle 30 may include a sharp distal tip 48, which may be disposed distal to the distal end 24 of the catheter 22. In some embodiments, the distal end 24 of the catheter 22 may include a distal opening 56, which may include a distalmost edge of the catheter 22. In some embodiments, the introducer needle 30 may extend through the distal opening 56.

In some embodiments, the introducer needle 30 may include the distal end 31, a proximal end, an introducer needle lumen 58 extending through the distal end of the introducer needle 30 and the proximal end of the introducer needle 30, and an inner surface 60 forming the introducer needle lumen 58. In some embodiments, a wall 61 of the introducer needle 30 that includes the inner surface 60 may not include a notch.

In some embodiments, the catheter 22 may include the distal end 24, the proximal end 26, a catheter lumen 62 extending through the distal end 24 and the proximal end 26, and an inner surface 64 forming the catheter lumen 62. In some embodiments, the distal end 24 of the catheter 22 may include one or more holes 66.

In some embodiments, a gap 68 may be disposed between an outer surface of the introducer needle 30 and the inner surface 64 of the catheter 22. In some embodiments, the gap 68 may be disposed within the catheter lumen 62. In some embodiments, the gap 68 may be in fluid communication with the holes 66 such that in response to the holes 66 being inserted into the vein 47, blood may flow through the holes 66 and into the gap 68. In some embodiments, all or a portion of the catheter 22 may be transparent, and the gap 68 may include a visualization channel in which blood flows and is visible to a clinician. In some embodiments, the gap 68 may be proximate the holes 66. In some embodiments, the gap 68 may be annular.

Figure 3:
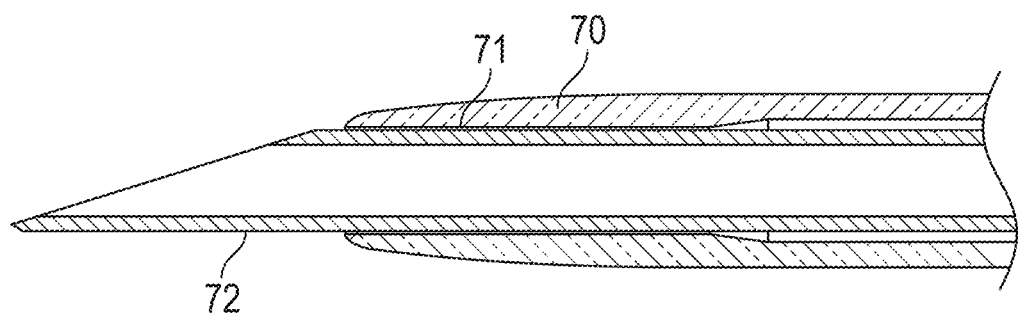
FIG. 3 is a cross-sectional view of another prior art catheter and another prior art introducer needle, disposed in the insertion position, according to some embodiments.

Referring now to FIG. 3, a prior art catheter 70 may be threaded onto a prior art introducer needle 72 such that blood does not enter the prior art catheter 70 at a distalmost end of the prior art catheter 70. This may prevent the clinician from accurately determining the prior art catheter 70 has entered a vein of the patient. In some embodiments, a land portion 71 of the prior art catheter 70 may be cylindrical.

Figure 4A:
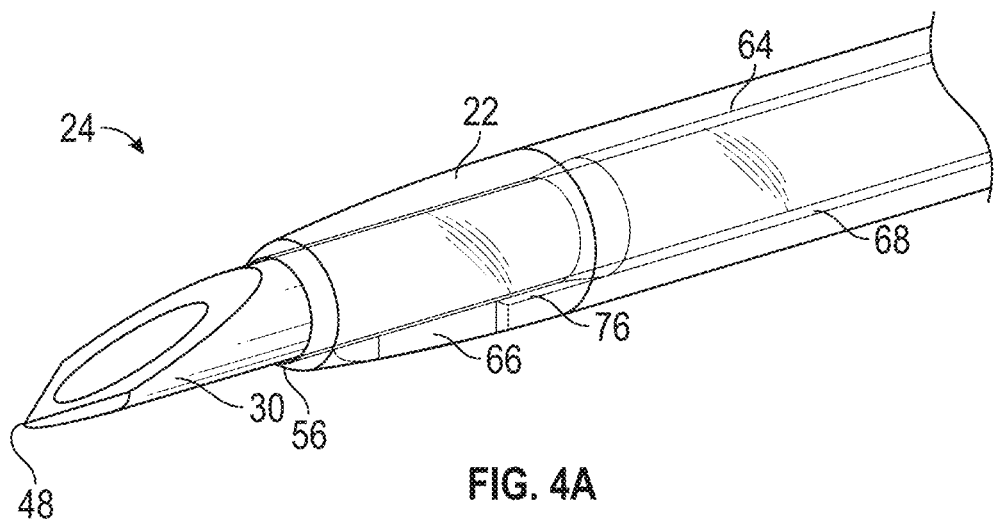
FIG. 4A is an upper perspective view of an example distal end of the catheter system of FIG. 1A, according to some embodiments.
Figure 4B:
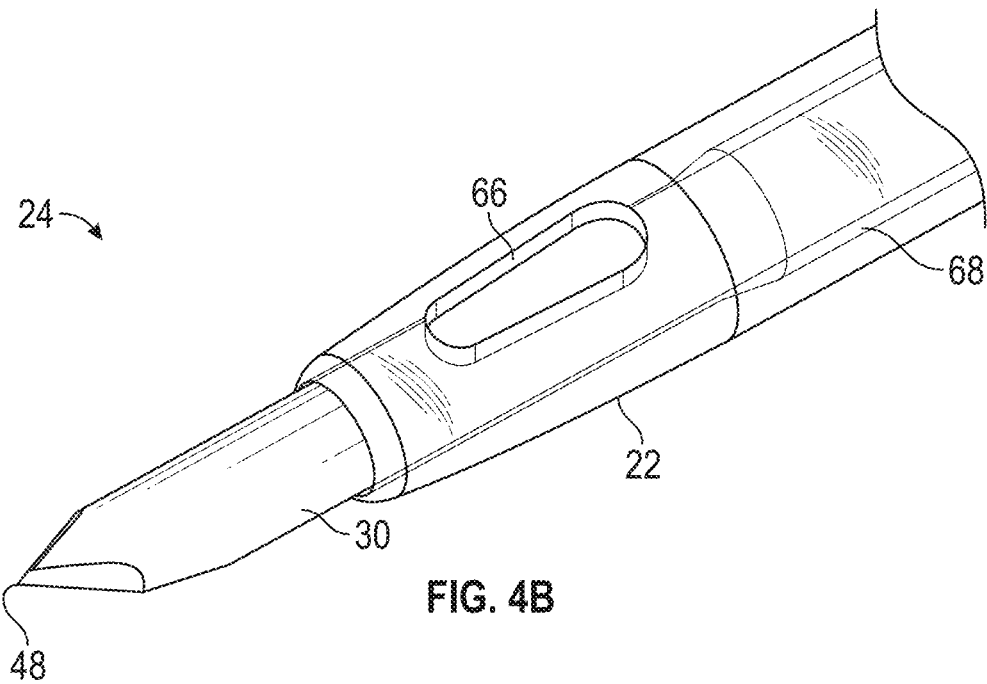
FIG. 4B is a lower perspective view of the distal end of FIG. 4A, according to some embodiments.
Figure 4C:
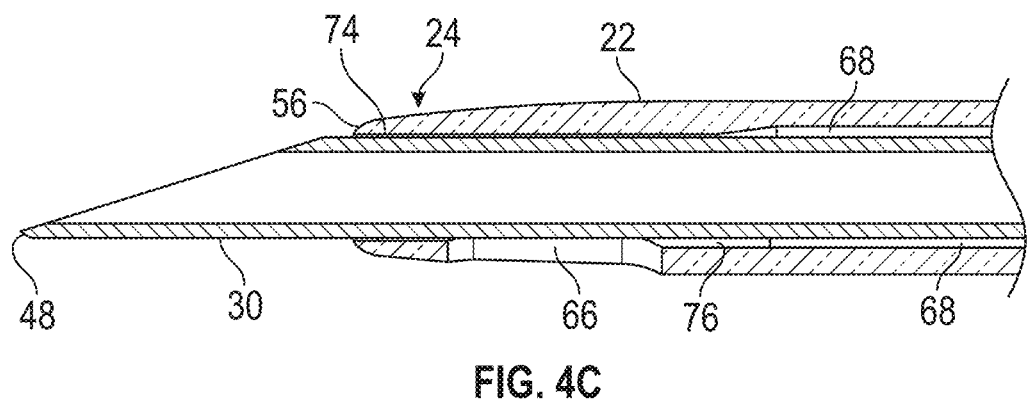
FIG. 4C is a cross-sectional view of the distal end of FIG. 4A, according to some embodiments.

Referring now to FIG. 4A-4C, in some embodiments, the inner surface 64 of the catheter 22 may include a land portion 74, which may be proximate the distal opening 56 and proximate the gap 68. In some embodiments, a diameter of the land portion 74 is approximately equal to an outer diameter of the introducer needle 30 such that the land portion 74 contacts the introducer needle 30. In some embodiments, a hole 66 may be disposed within the land portion 74 and a clearance 76 may connect the gap 68 to the hole 66. In some embodiments, the hole 66 and/or the gap 68 may be disposed on a top of the catheter 22 opposite the sharp distal tip 48. In some embodiments, the hole 66 and/or the gap 68 may be disposed on a bottom of the catheter 22, on a same side as the sharp distal tip 48, which may facilitate quick identification that the catheter 22 is in the vein. In some embodiments, the hole 66 and/or the gap 68 may be disposed in between the top and the bottom of the catheter 22.

Figure 5A:
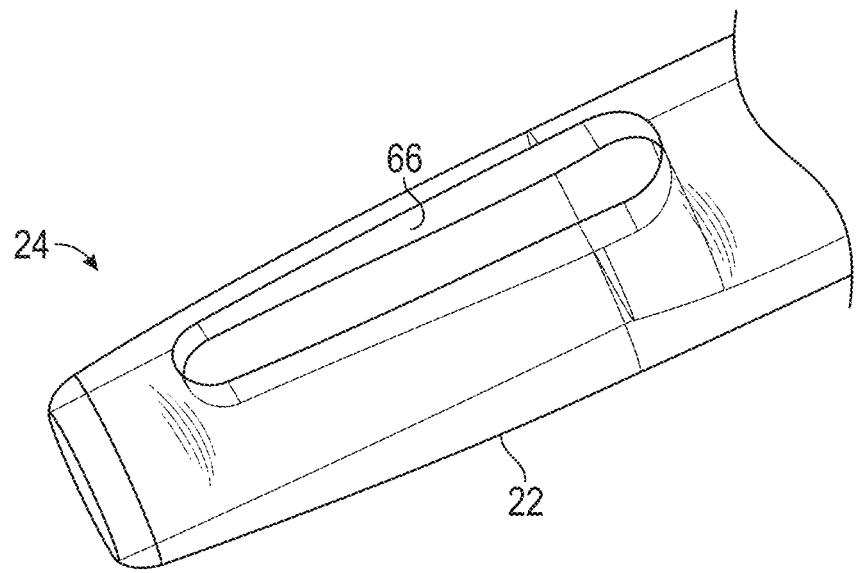
FIG. 5A is a lower perspective view of a distal end of another example catheter, according to some embodiments.
Figure 5B:
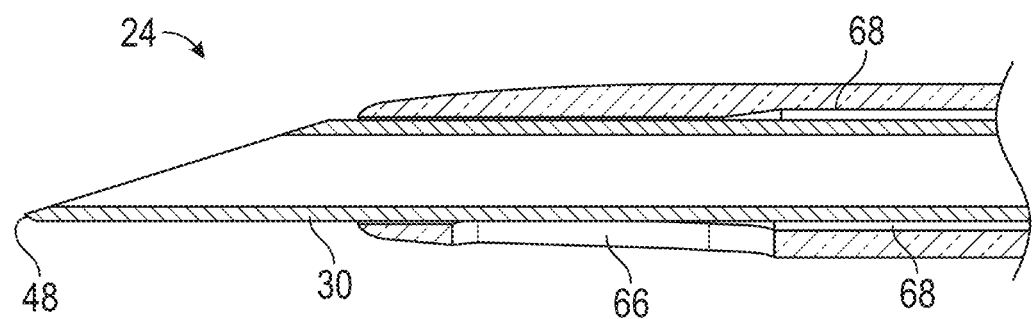
FIG. 5B is a cross-sectional view of another example distal end of the catheter system of FIG. 1A, according to some embodiments.

Referring now to FIG. 5A-5B, in some embodiments, the hole 66 may be elongated and a proximal end of the hole 66 may be disposed proximal to the land portion 74. In these and other embodiments, the clearance 76 (see, for example, FIG. 4C) may not be present. In some embodiments, the hole 66 may be proximate the gap 68.

Figure 6A:
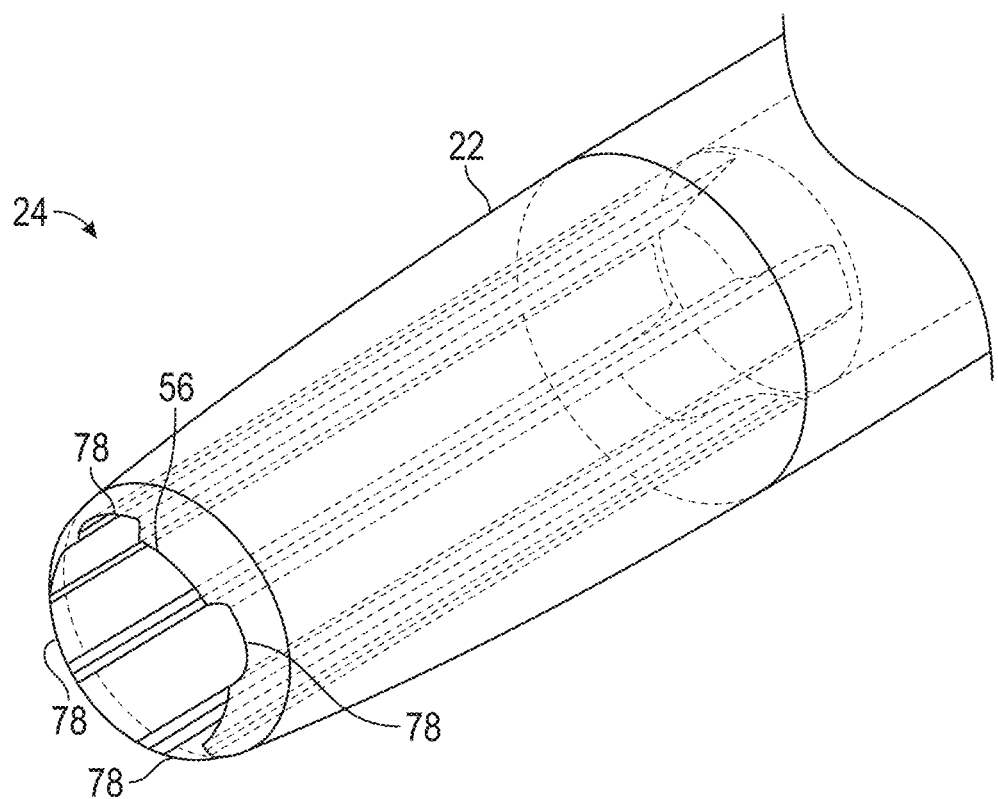
FIG. 6A is an upper perspective view of a distal end of another example catheter, according to some embodiments.
Figure 6B:
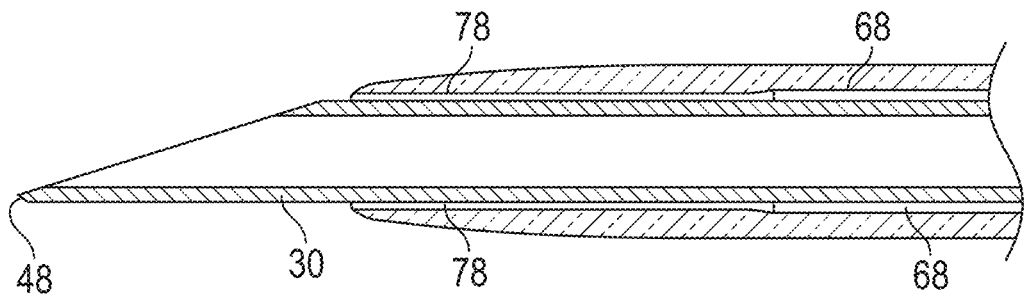
FIG. 6B is a cross-sectional view of another example distal end of the catheter system of FIG. 1A, illustrating the catheter of FIG. 6A, according to some embodiments.

Referring now to FIGS. 6A-6B, in some embodiments, the inner surface 64 of the catheter 22 may include one or more channels 78, which may extend from the distal opening 56. In some embodiments, the channels 78 may be configured to allow blood to flow between the outer surface of the introducer needle 30 and the inner surface 64 of the catheter 22 in response to the distal end 24 of the catheter 22 being inserted into the vein. In some embodiments, the blood may flow from the vein, through the channels 78, and into the gap 68. In some embodiments, a portion of the distal opening 56 in between the channels 78 may contact the introducer needle 30.

Figure 7A:
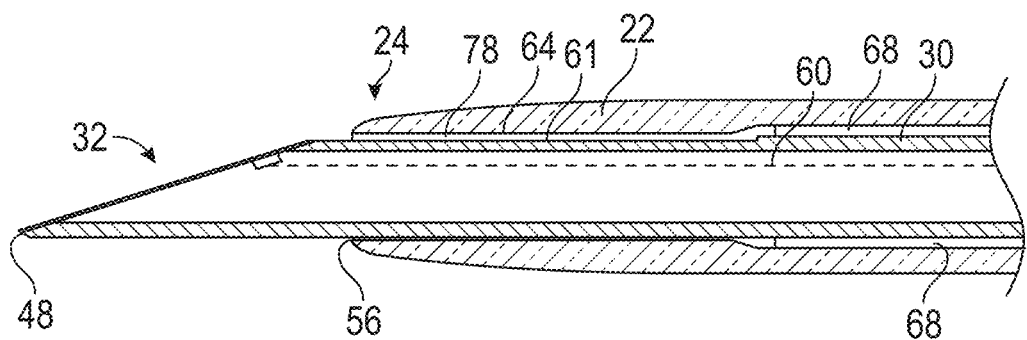
FIG. 7A is a cross-sectional view of another example distal end of the catheter system of FIG. 1A, illustrating an example sensor, according to some embodiments.

Referring now to FIG. 7A, in some embodiments, a catheter system, such as for example, the catheter system 10 of FIGS. 1A-1B, may include one or more sensors 80. In some embodiments, the sensors 80 may be embedded in the inner surface 60 of the introducer needle 30 at the distal end 31 of the introducer needle 30. In some embodiments, the sensors 80 may be proximate the introducer needle lumen 58 and configured to contact blood travelling into the introducer needle 30.

In some embodiments, the sensors 80 may be configured to detect the distal end 31 of the introducer needle 30 is within the vein. In some embodiments, the sensors 80 may be configured to detect the distal end 31 of the introducer needle 30 is withdrawn and/or partially withdrawn from the vein. In some embodiments, the sensors 80 may include bio-impedance sensors, pressure sensors, capacitance sensors, infrared sensors, or another suitable type of sensor. In some embodiments, a pattern or arrangement of the sensors 80 may vary.

In some embodiments, the sensors 80 may be coupled to one or more leads 86, which may be embedded in the introducer needle 30. In some embodiments, the leads 86 may connect the sensors 80 to a monitor, which may include a processor. It is understood that the sensors 80 may be combined with any of the embodiments of the present application, which may facilitate detection of the catheter 22 within the vein after detection of the introducer needle 30 within the vein via the sensors 80.

Figure 7B:
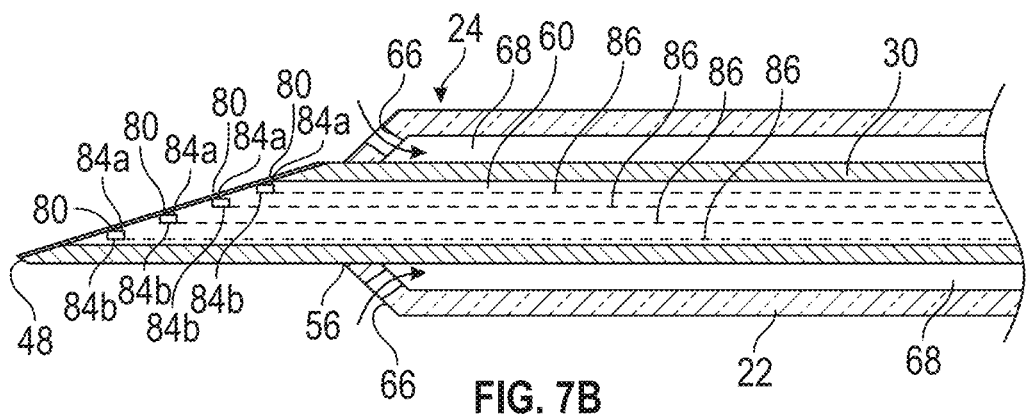
FIG. 7B is a cross-sectional view of another distal end of the catheter system of FIG. 1A, according to some embodiments.
Figure 7C:
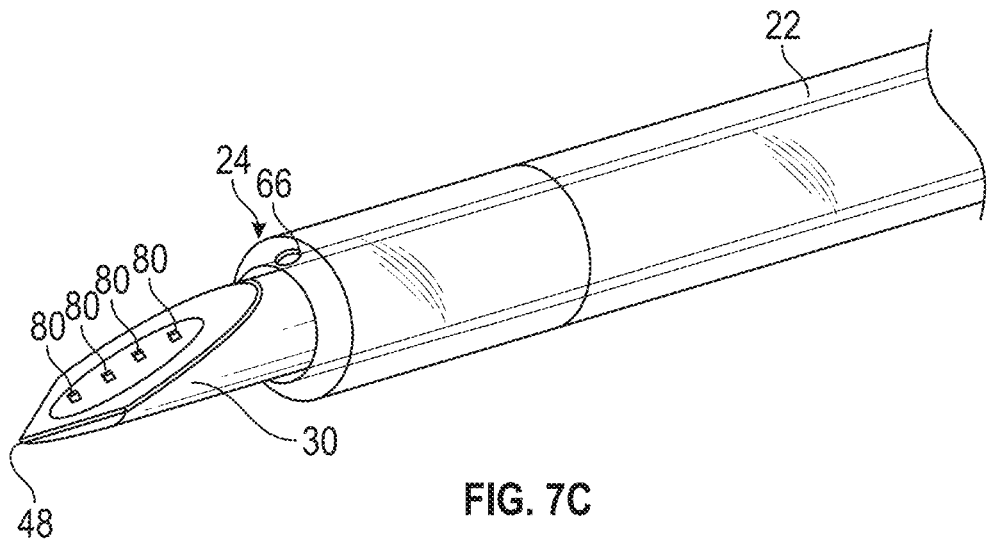
FIG. 7C is an upper perspective view of the distal end of FIG. 7B, according to some embodiments.
Figure 7D:
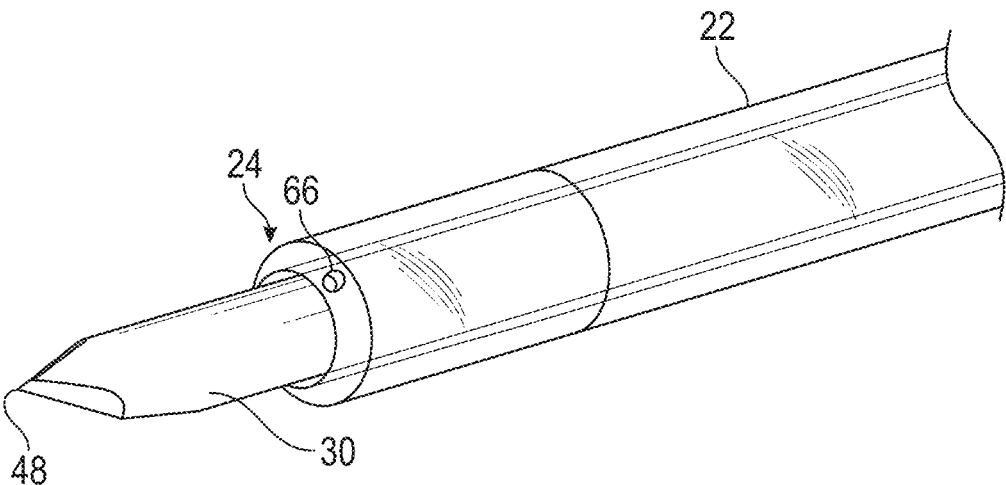
FIG. 7D is a lower perspective view of the distal end of FIG. 7B, according to some embodiments.

Referring now to FIG. 7B-7D, multiple sensors 80 are illustrated, according to some embodiments. In some embodiments, the sensors 80 may include bio-impedance sensors, which may each include two or more electrodes 84. In some embodiments, a particular bio-impedance sensor may include a first electrode 84a and a second electrode 84b (which may be referred to collectively as "electrodes 84"). In some embodiments, the electrodes 84 may be separated by a distance in generally perpendicular to a longitudinal axial direction. In some embodiments, an orientation or direction of the distance separating the electrodes 84 may vary.

In some embodiments, during advancement of the introducer needle 30 into the patient, a current may be applied to the bio-impedance sensors, and an impedance across the electrodes 84 may be measured continuously. In some embodiments, it may be determined that the distal end 31 of the introducer needle 30 is disposed within the vein based on the impedance that is measured between the electrodes 84. In some embodiments, in response to the impedance that is measured being above or below a threshold value or a change in the impedance that is measured being above another threshold value, it may be determined that the distal end 31 of the introducer needle 30 is disposed within the vein.

In some embodiments, in response to a determination that the distal end 31 of the introducer needle 30 is disposed within the vein, an alert may be provided on the catheter system or elsewhere. In some embodiments, in response to a determination that the distal end 31 of the introducer needle 30 is withdrawn or partially withdrawn from the vein, the alert may be provided on the catheter system or elsewhere. In some embodiments, the alert may include a visual or audible alert. In some embodiments, the alert may include a light, an example of which may be described later with respect to FIG. 14.

In some embodiments, the sensors 80 may be aligned with a bevel of the distal end 31 of the introducer needle 30. In some embodiments, the sensors 80 may be staggered or spaced apart in the longitudinal axial direction. In some embodiments, one or more sensors 80 may be disposed proximally to one or more other sensors 80. In some embodiments, the placement of the sensors 80 may facilitate identification by the clinician of a depth at which the introducer needle 30 and/or the catheter 22 is inserted in the vein. In some embodiments, the clinician may remove the introducer needle 30 from the catheter 22 in response to detection by one or more of the sensors 80 that the catheter 22 is within the vein.

Figure 7E:
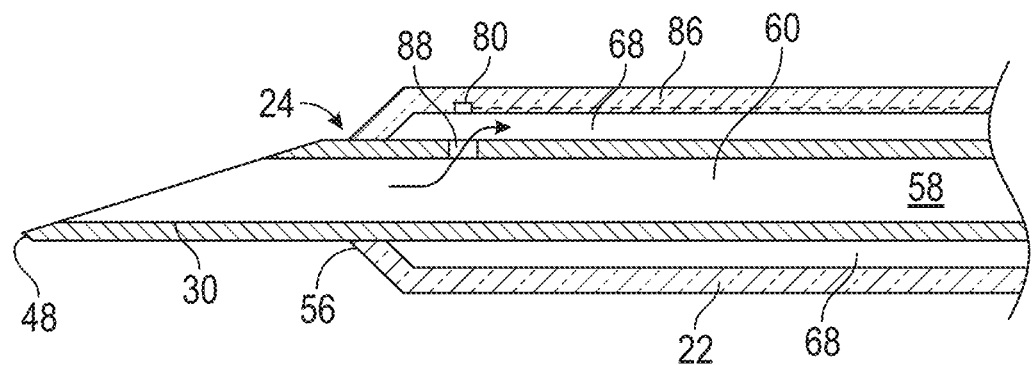
FIG. 7E is a cross-sectional view of another example distal end of the catheter system of FIG. 1A, according to some embodiments.

Referring now to FIG. 7E, in some embodiments, the sensors 80 may be embedded in the outer surface of the catheter 22 at the distal end 24 of the catheter 22 and proximate the gap 68. In some embodiments, the introducer needle 30 may include a notch 88, which may be disposed adjacent and/or proximate the distal opening 56. In some embodiments, the sensors 80 may be configured to contact blood in the vein when the catheter 22 is within the vein.

In some embodiments, the sensors 80 may be staggered or spaced apart in the longitudinal axial direction. In some embodiments, one or more sensors 80 may be disposed proximally to one or more other sensors 80. In these embodiments, the placement of the sensors 80 may facilitate identification by the clinician of a depth at which the catheter 22 is inserted in the vein. In these embodiments, the sensors 80 may facilitate confirmation of one or more positions of the catheter 22 with respect to the vein, such as, for example, the positions discussed with respect to FIG. 14 or the catheter 22 has entered the vein, the catheter 22 is fed further into the vein, and the catheter is fully inserted into the vein. In some embodiments, multiple sensors 80 may be embedded in the outer surface of the catheter 22 or a single sensor 80 may be imbedded in the outer surface of the catheter 22.

In some embodiments, the sensors 80 may be configured to detect the distal end 24 of the catheter 22 is within the vein. In some embodiments, the sensors 80 may be configured to detect the distal end 24 of the catheter 22 is withdrawn or partially withdrawn from the vein. In some embodiments, during advancement of the catheter 22 and the introducer needle 30 into the patient, a current may be applied to the bio-impedance sensors, and the impedance across the electrodes 84 may be measured continuously. In some embodiments, it may be determined that the distal end 24 of the catheter 22 is disposed within the vein based on the impedance that is measured between the electrodes 84.

In some embodiments, in response to the impedance that is measured being above or below a threshold value or a change in the impedance that is measured being above another threshold value, it may be determined that the distal end 24 of the catheter 22 is disposed within the vein. In some embodiments, in response to a determination that the distal end 24 of the catheter 22 is disposed within the vein, the alert may be provided on the catheter system or elsewhere. In some embodiments, in response to a determination that the distal end 24 of the catheter 22 is withdrawn or partially withdrawn, the alert may be provided on the catheter system or elsewhere.

Figure 7F:
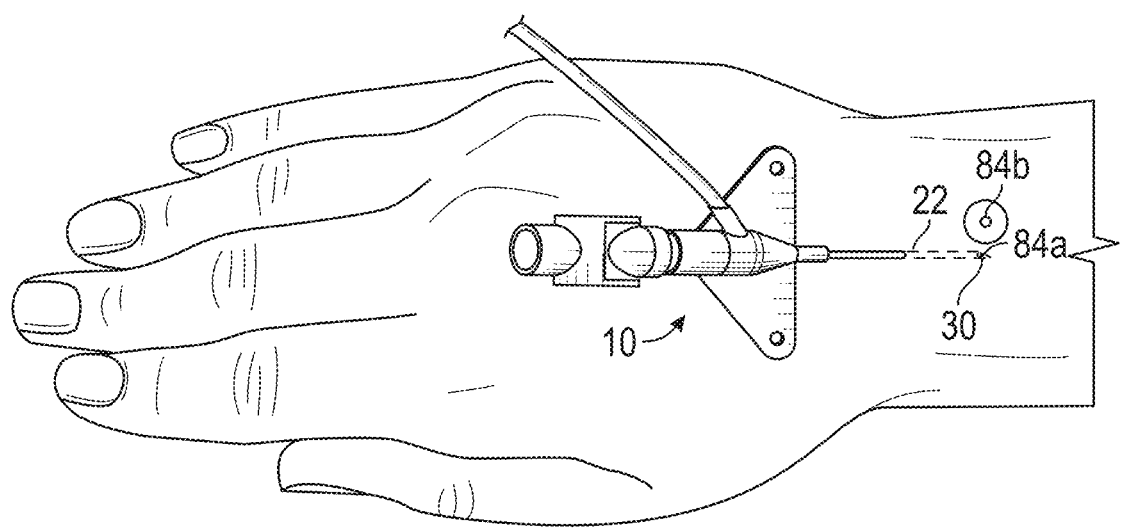
FIG. 7F is an upper perspective view of the catheter system of FIG. 1A inserted into a patient, illustrating an example sensor, according to some embodiments.

Referring now to FIG. 7F, in some embodiments, a particular sensor 80 may include a bio-impedance sensor, which may include the first electrode 84a and the second electrode 84b. In some embodiments, the first electrode 84a may be embedded in the inner surface 64 of the introducer needle 30 at the distal end 31 of the introducer needle 30 or embedded in the in the outer surface of the catheter 22 at the distal end 24 and proximate the gap 68. In some embodiments, the second electrode 84b may be configured to be secured to skin of a patient as a reference point.

In some embodiments, in response to the impedance that is measured between the electrodes 84 being above or below a threshold value or a change in the impedance that is measured being above another threshold value, it may be determined that the introducer needle 30 and/or the catheter 22 is disposed within the vein.

Figure 8A:
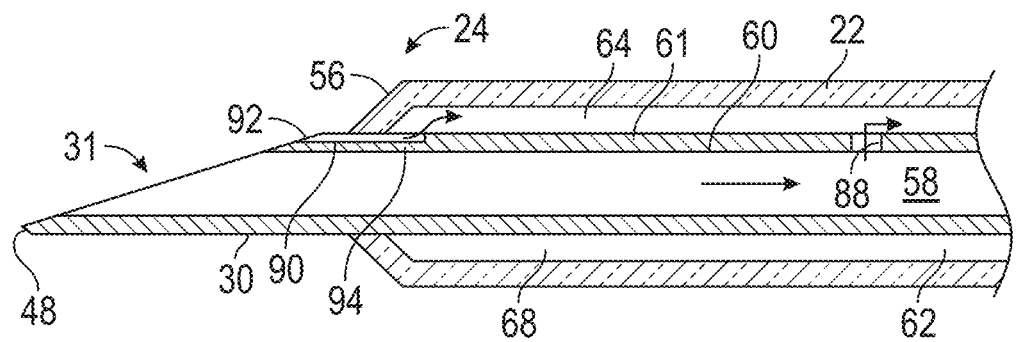
FIG. 8A is a cross-sectional view of another example distal end of the catheter system of FIG. 1A, according to some embodiments.

Referring now to FIG. 8A, in some embodiments, the introducer needle 30 may include the notch 88. In some embodiments, the outer surface of the introducer needle 30 may include a channel 90 distal to the notch 88. In some embodiments, a distal end 92 of the channel 90 may be disposed distal to the distal opening 56. In some embodiments, a proximal end 94 of the channel 90 may be disposed proximal to the distal opening 56 and/or proximate the gap 68. In some embodiments, the gap 68 may be in fluid communication with the channel 90 such that in response to the distal end 92 of the channel 90 being inserted into the vein, blood may flow through the channel 90 and into the gap 68. In some embodiments, the notch 88 may be proximate the gap 68. In some embodiments, the gap 68 may be in fluid communication with the channel 90 and the notch 88.

In some embodiments, the notch 88 and the channel 90 may facilitate visualization of two blood flashbacks by the clinician, one indicating insertion of the introducer needle 30 within the vein, and the other indicating insertion of the catheter 22 within the vein. In some embodiments, the notch 88 may be disposed more proximally than the notch 50 of the prior art introducer needle 46 (illustrated, for example, in FIG. 2A), which may prevent confusion of the two blood flashbacks by the clinician. In some embodiments, the notch 88 may be positioned at a middle or towards a proximal end of the introducer needle 30. In some embodiments, a length of the channel 90 may be adjusted such that blood flowing through the channel 90 indicates the introducer needle 30 is hooded. In some embodiments, the notch 88 may be positioned within the catheter adapter 16.

Figure 8B:
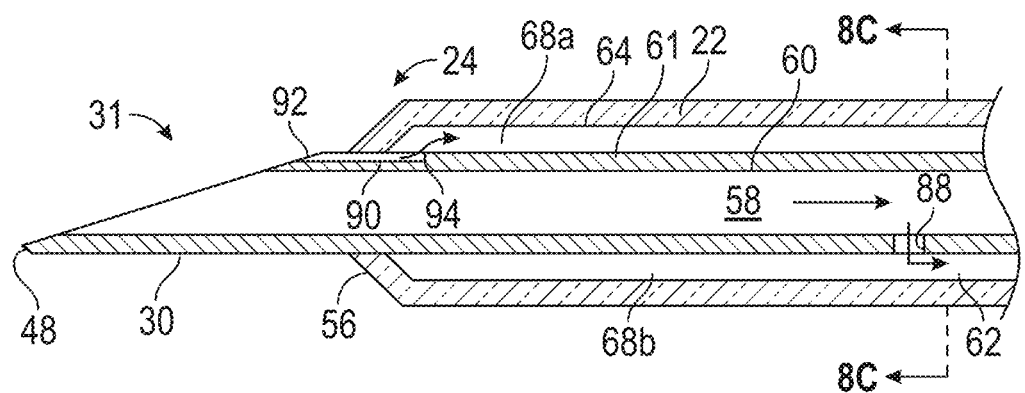
FIG. 8B is a cross-sectional view of another example distal end of the catheter system of FIG. 1A, according to some embodiments.
Figure 8C:
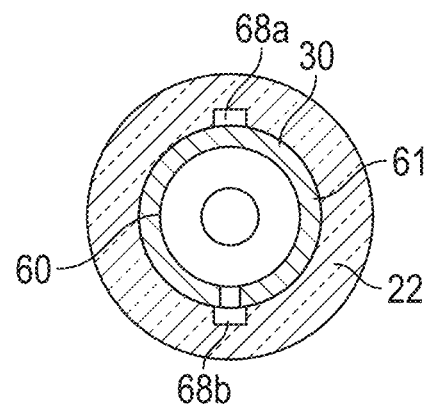
FIG. 8C is a cross-sectional view of the distal end of FIG. 8B along the line 8C-8C of FIG. 8B, according to some embodiments.

Referring now to FIGS. 8B-8C, in some embodiments, a first gap 68a may be separated from a second gap 68b. In some embodiments, the second gap 68b may also be disposed between the outer surface of the introducer needle 30 and the inner surface 64 of the catheter 22. In some embodiments, the second gap 68b may be disposed within the catheter lumen 62. In some embodiments, the second gap 68b may be in fluid communication with the notch 88 such that in response to the introducer needle 30 being inserted into the vein, the blood may flow into the introducer needle 30 and out the notch 88 into the second gap 68b. In some embodiments, the first gap 68a and the second gap 68b may prevent confusion between an indication the catheter 22 is within the vein and an indication the introducer needle 30 is within the vein.

Figure 8D:
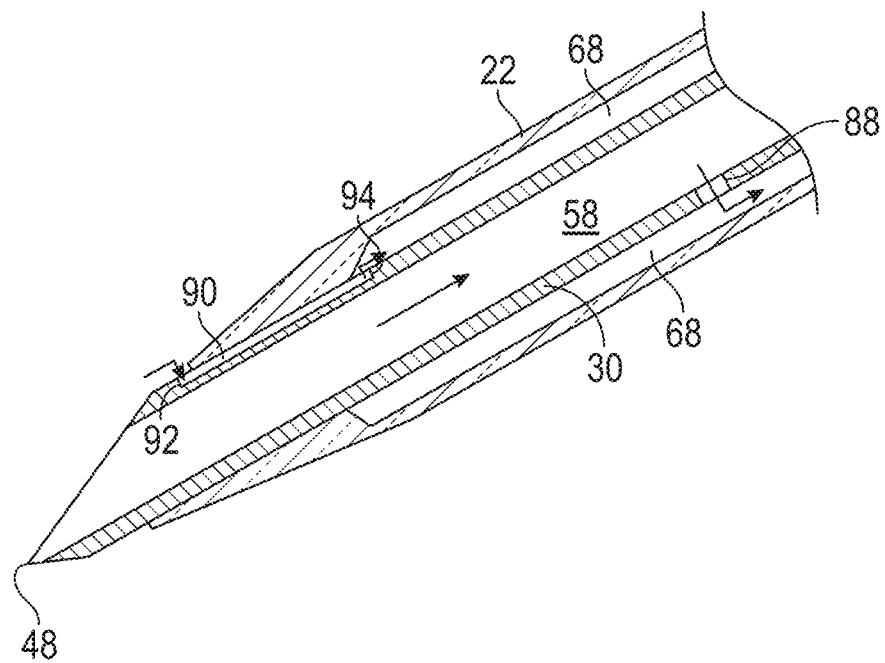
FIG. 8D is cross-sectional view of another example distal end of the catheter system of FIG. 1A, according to some embodiments.

Referring now to FIG. 8D, in some embodiments, the catheter 22 may be asymmetrical. An example asymmetrical catheter is described in U.S. patent application Ser. No. 15/286,261, filed Oct. 5, 2016, entitled "CATHETER WITH AN ASYMMETRIC TIP," which is hereby incorporated by reference in its entirety.

Figure 9A:
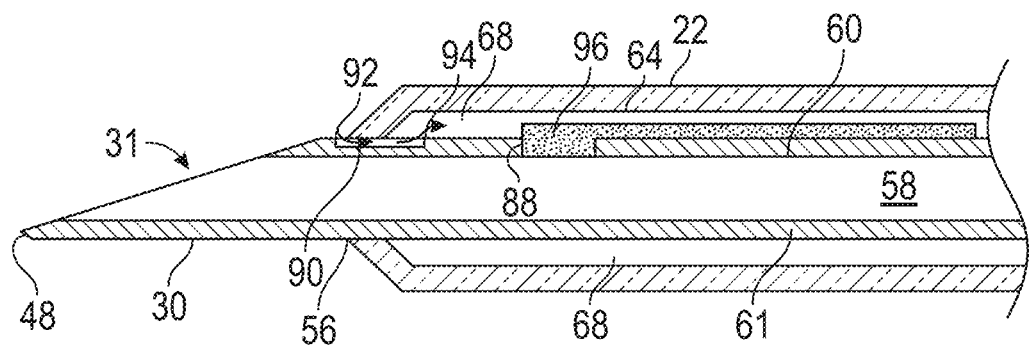
FIG. 9A is cross-sectional view of another example distal end of the catheter system of FIG. 1A, illustrating an example absorbent material, according to some embodiments.

Referring now to FIG. 9A, in some embodiments, an absorbent material 96 may be disposed within the notch 88 and/or may extend proximally within the gap 68. In some embodiments, the absorbent material 96 may be porous. In some embodiments, the absorbent material 96 may turn red when contacted with blood, providing a quick indication of penetration of the vein by the introducer needle 30. In some embodiments, the absorbent material 96 may prevent blood that exited the notch 88 from flowing distally in the gap 68, which may prevent comingling of blood travelling proximally through the channel 90 and blood exiting the notch 88, facilitating easy differentiation and determination of a time to thread the catheter 22 off the introducer needle 30.

Figure 9B:
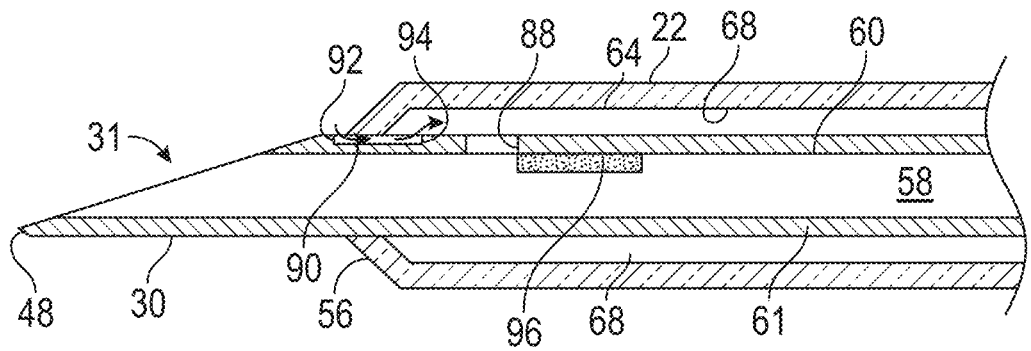
FIG. 9B is a cross-sectional view of another example distal end of the catheter system of FIG. 1A, illustrating the absorbent material in a first position, according to some embodiments.
Figure 9C:
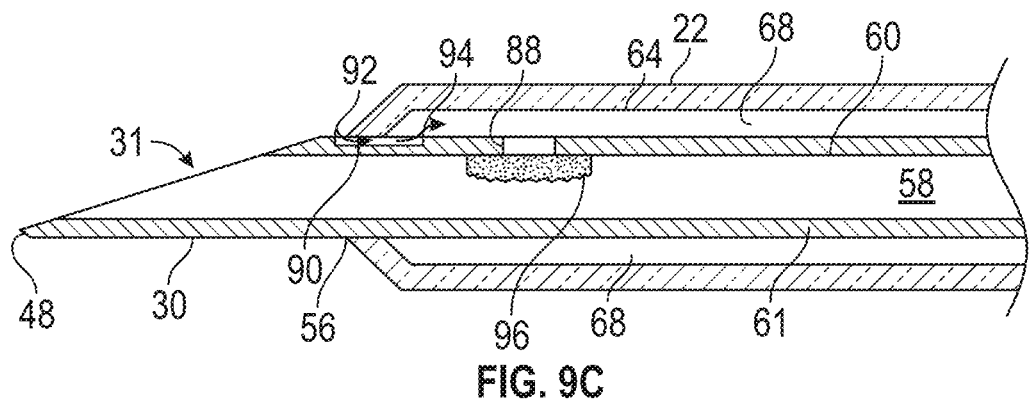
FIG. 9C is a cross-sectional view of the distal end of FIG. 9B, illustrating the absorbent material in a second position, according to some embodiments.

Referring now to FIG. 9B-9C, in some embodiments, the absorbent material 96 may be disposed within the introducer needle lumen 58 and proximal to the notch 88. In some embodiments, the absorbent material 96 may extend along the outer surface of the introducer needle 30.

In some embodiments, the absorbent material 96 may be porous. FIG. 9B illustrates the absorbent material 96 prior to contact by blood, according to some embodiments. FIG. 9C illustrates the absorbent material after contact with blood, according to some embodiments.

In some embodiments, in response to blood contacting the absorbent material 96, the absorbent material 96 may expand or swell and cover the notch 88. In some embodiments, covering of the notch 88 by the absorbent material 96 may close off the notch 88 after some initial blood flows through the notch 88 into the gap 68. In some embodiments, closing off the notch 88 may prevent comingling of blood travelling proximally through the channel 90 and blood within the introducer needle 30, facilitating easy differentiation and determination of a time to thread the catheter 22 off the introducer needle 30.

Figure 10A:
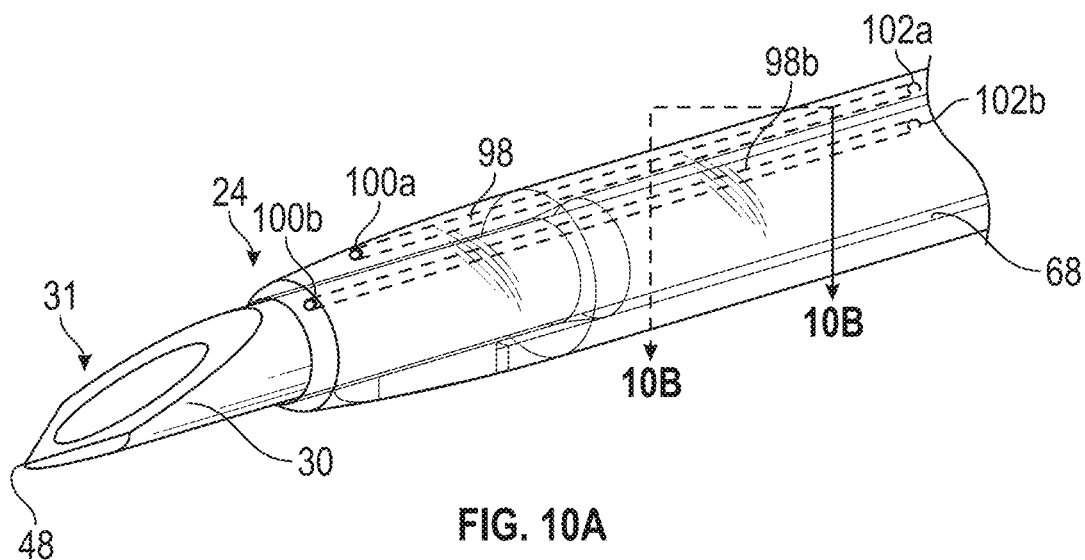
FIG. 10A is an upper perspective view of another example distal end of the catheter system of FIG. 1A, according to some embodiments.
Figure 10B:
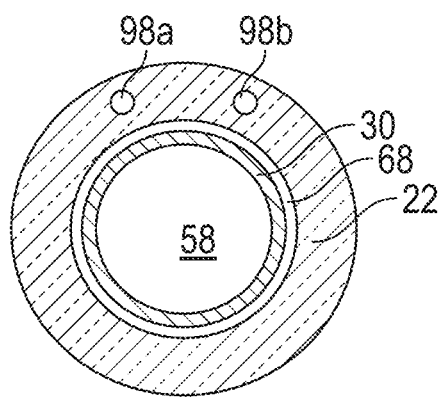
FIG. 10B is a cross-sectional view of the distal end of FIG. 10A along the line 10B-10B of FIG. 10A, according to some embodiments.
Figure 10C:
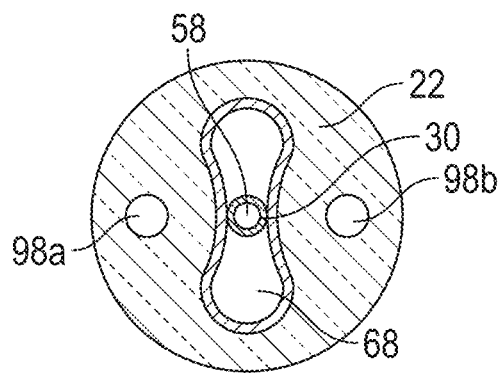
FIG. 10C is a cross-sectional view of another example distal end of the catheter system of FIG. 1A, according to some embodiments.

Referring now to FIG. 10, in some embodiments, the catheter 22 may include multiple lumens. For example, the catheter 22 may include the catheter lumen 62 and one or more other lumens 98. In some embodiments, the other lumens 98 may be disposed within a wall of the catheter 22. In some embodiments, a distal end of each of the other lumens 98 may include an aperture 100, which may extend through a portion of the wall of the catheter 22. In some embodiments, a proximal end of each of the other lumens 98 may include another aperture 102, which may empty into the gap 68 and allow venting of the other lumens 98.

In some embodiments, the catheter lumen 62 may be larger than the other lumens 98 to facilitate infusion therapy through the catheter lumen 62. In some embodiments, the other lumens 98 may be disposed on the top of the catheter 22 opposite the sharp distal tip 48, which may facilitate visualization of blood within the other lumens 98. In some embodiments, the other lumens 98 may be disposed on a bottom of the catheter 22. In some embodiments, the other lumens 98 may be disposed in between the top and the bottom of the catheter 22, which may also facilitate visualization of blood within the other lumens 98.

In some embodiments, the apertures 100 and/or the other lumens 98 may be staggered or spaced apart in the longitudinal axial direction. For example, a first aperture 100a and/or a first other lumen 98a may be disposed proximal to a second aperture 100b and/or a second other lumen 98b, as illustrated, for example, in FIG. 10A. In some embodiments, the spacing of the apertures 100 may facilitate identification by the clinician of a depth at which the catheter 22 is inserted in the vein. In some embodiments, the clinician may remove the introducer needle 30 from the catheter 22 in response to visualization of blood in one or more of the other lumens 98.

Figure 11A:
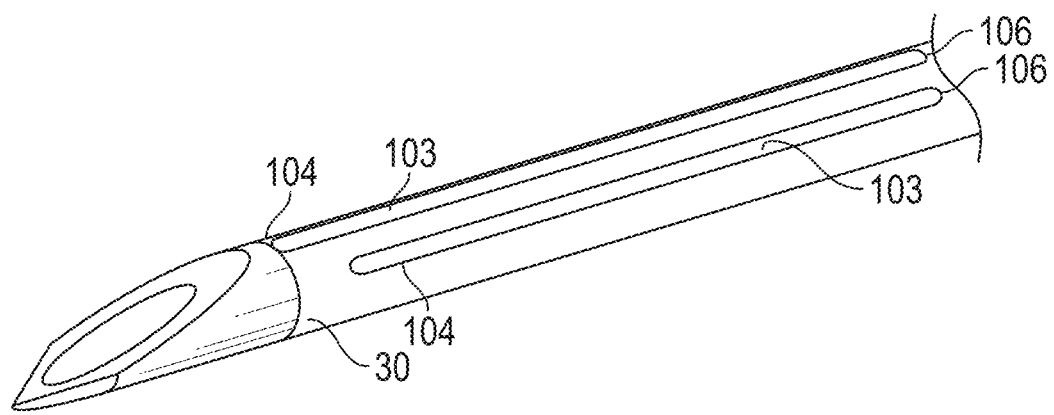
FIG. 11A is an upper perspective view of an example introducer needle, according to some embodiments.
Figure 11B:
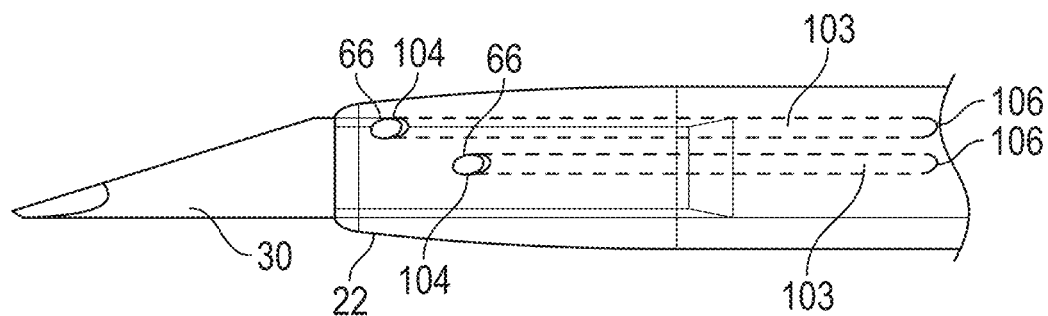
FIG. 11B is an upper perspective view of another example distal end of the catheter system of FIG. 1A, illustrating the introducer needle of FIG. 11A, according to some embodiments.

Referring now to FIGS. 11A-11B, in some embodiments, the introducer needle 30 may include one or more grooves 103. In some embodiments, a distal end 104 of each of the grooves 103 may be proximate a particular hole 66, which may extend through the wall of the catheter 22. In some embodiments, the gap 68 may be disposed within a particular groove 103. In some embodiments, a proximal end 106 of each of the holes 66 may be aligned with the gap 68.

In some embodiments, the holes 66 may be arranged such that some of the holes 66 are distal to other of the holes 66. In some embodiments, the holes 66 and/or the grooves 103 may be staggered or spaced apart in the longitudinal axial direction. In some embodiments, the spacing of the holes 66 may facilitate identification by the clinician of a depth at which the catheter 22 is inserted in the vein. In some embodiments, the clinician may remove the introducer needle 30 from the catheter 22 in response to visualization of blood in one or more of the grooves 103.

In some embodiments, the grooves 103 may be disposed on the top of the catheter 22 opposite the sharp distal tip 48, which may facilitate visualization of blood within the grooves 103. In some embodiments, the grooves 103 may be disposed on a bottom of the catheter 22. In some embodiments, the grooves 103 may be disposed in between the top and the bottom of the catheter 22, which may also facilitate visualization of blood within the grooves 103.

Figure 12:
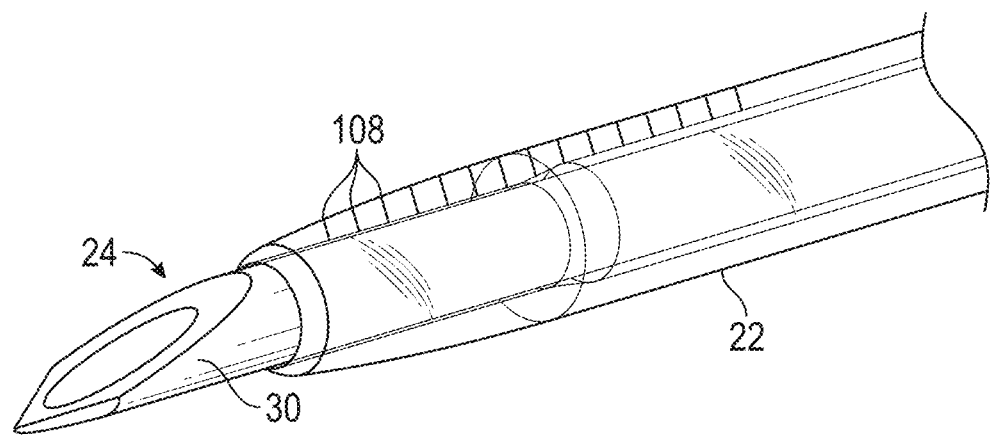
FIG. 12 is an upper perspective view of an example catheter, illustrating multiple markings on the catheter, according to some embodiments.

Referring now to FIG. 12, in some embodiments, an outer surface of the catheter 22 may include one or more markings 108, which may be graduated, and which may indicate to the clinician a depth of insertion of the catheter 22 into the vein. In some embodiments, the clinician may advance the catheter 22 several markings 108 before threading off the catheter 22 from the introducer needle 30. In some embodiments, the markings 108 may be evenly spaced apart. In some embodiments, the markings 108 may include lines generally perpendicular to a longitudinal axis of the catheter 22. In some embodiments, the clinician may insert the catheter 22 such that a particular marking 108 is aligned or even with an outer surface of skin of the patient. In some embodiments, in response to the particular marking 108 being aligned with skin of the patient, that may indicate to the clinician that the catheter 22 is inserted into the vein. In further detail, in response to the particular marking 108 being aligned with skin of the patient, that may indicate to the clinician that the catheter 22 has entered the vein or that the catheter 22 is fully inserted within the vein. In some embodiments, the catheter 22 may enter the vein when the vein wall is fully penetrated by the catheter 22. In some embodiments, the catheter 22 may be fully inserted into the vein when the catheter 22 is ready for use, such as in infusion or blood draw.

In some embodiments, in response to a first of the markings 108 being aligned with the outer surface of the skin of the patient, the catheter 22 may be inserted into the vein a first amount or a first depth, which may correspond to entrance of the catheter 22 into the vein. In some embodiments, in response to a second of the markings 108 being aligned with the outer surface of the skin of the patient, the catheter 22 may be inserted to a second amount or a second depth, which may correspond to full insertion of the catheter 22 within the vein. In some embodiments, the second of the markings 108 may be proximal to the first of the markings 108.

In some embodiments, a particular catheter system may include one or more of the following: a first position indicator, a second position indicator, and a third position indicator. In some embodiments, the first position indicator may include the notch 50, the notch 88, the absorbent material 96, or one or more sensors 80 of one or more of the previous Figures. In some embodiments, blood flowing through or contacting the first position indicator may indicate to the clinician that introducer needle 30 is inserted into the vein. In some embodiments, insertion of the introducer needle 30 into the vein may include entrance of the introducer needle 30 into the vein or penetration of the vein wall by the introducer needle 30.

In some embodiments, the second position indicator may include one or more holes 66 in the catheter 22 in fluid communication with the gap 68, one or more channels 78 in fluid communication with the gap 68, one or more sensors 80 within the catheter 22, one or more channels 90 in fluid communication with the gap 68, one or more other lumens 98 in fluid communication with a particular aperture 100, one or more grooves 103 each proximate a particular hole 66, or one or more markings 108 of one or more of the previous Figures. In some embodiments, the second position indicator may include the first of the markings 108 and alignment of the second position indicator with the outer surface of the skin of the patient may indicate to the clinician that catheter 22 is inserted within the vein the first amount or the first depth. In some embodiments, blood flowing through or contacting the second position indicator may indicate to the clinician that the catheter 22 is inserted into the vein the first amount or the first depth. In some embodiments, in response to blood flowing through or contacting the second position indicator or alignment of the second position indicator with the outer surface of the skin, the catheter 22 may be inserted within the vein the first amount or the first depth.

In some embodiments, the third position indicator may include one or more holes 66 in the catheter 22 in fluid communication with the gap 68, one or more sensors 80 within the catheter 22, one or more other lumens 98 in fluid communication with a particular aperture 100, one or more grooves 103 each proximate a particular hole 66, or one or more markings 108 of one or more of the previous Figures. In some embodiments, the third position indicator may include the second of the markings 108 and alignment of the third position indicator with the outer surface of the skin of the patient may indicate to the clinician that catheter 22 is inserted within the vein the second amount or the second depth. In some embodiments, blood flowing through or contacting the third position indicator may indicate the catheter 22 is inserted into the vein the second amount or the second depth. In some embodiments, in response to blood flowing through or contacting the third position indicator or alignment of the third position indicator with the outer surface of the skin, the catheter 22 may be inserted within the vein the second amount or the second depth.

Figure 13:
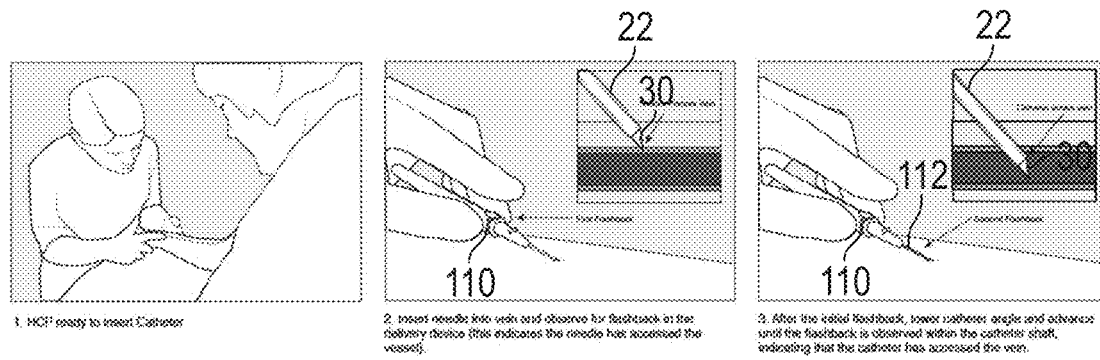
FIG. 13 is a diagram of an example catheter insertion method, according to some embodiments.

Referring now to FIG. 13, in some embodiments, the clinician may observe a first blood flashback 110 corresponding to entry of the introducer needle 30 into the vein, followed by a second blood flashback 112 corresponding to entry of the catheter 22 into the vein. In some embodiments, the first blood flashback 110 may be visualized by the clinician in a flash chamber or another suitable location within a catheter system. In some embodiments, the second blood flashback 112 may be visualized by the clinician in a gap between the catheter 22 and the introducer needle 30, such as, for example, the gap 68 discussed with respect to at least FIGS. 2B and 4-10 of the present application.

Figure 14:
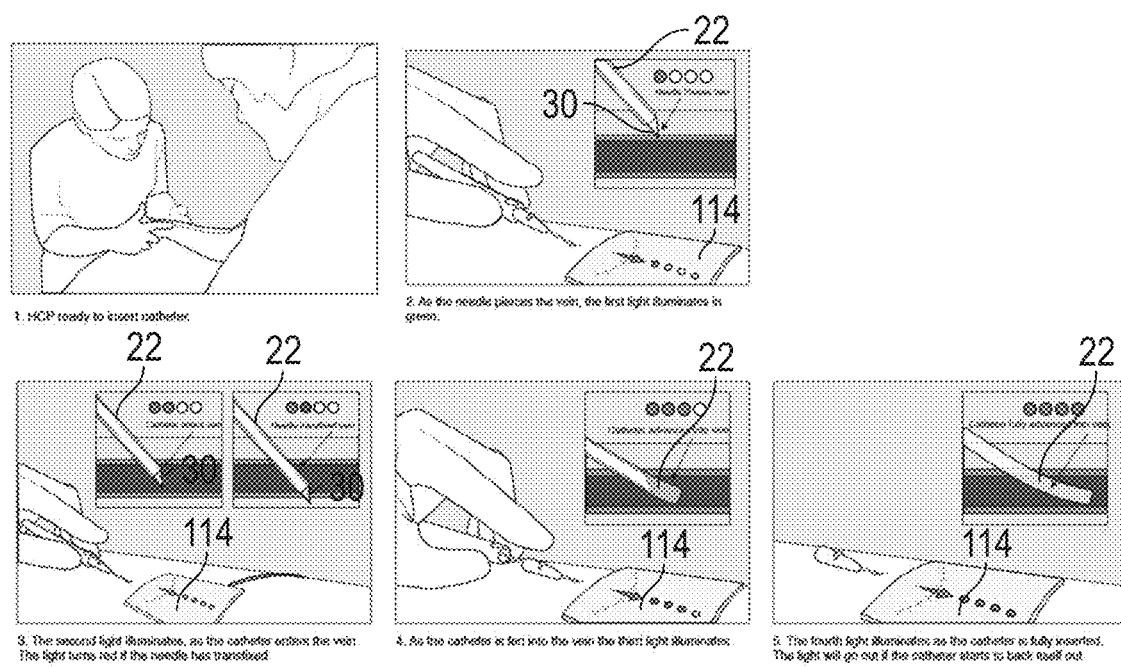
FIG. 14 is a diagram of another catheter insertion method and an alert patch, according to some embodiments.

Referring now to FIG. 14, in some embodiments, an alert patch 114 may be adhered to the skin of the patient. In some embodiments, the alert patch 114 may be configured to provide the alert, which may be described further with respect to FIGS. 7B-7D. In some embodiments, the alert patch 114 may be configured to provide a particular alert based on a phase of insertion of a catheter assembly into the patient.

In some embodiments, the alert patch 114 may be configured to provide one or more of the following alerts: a first alert, a second alert, a third alert, and a fourth alert. In some embodiments, the alert patch 114 may be configured to provide the first alert in response to the introducer needle 30 piercing or entering the vein. In some embodiments, the alert patch 114 may be configured to provide the second alert in response to the catheter 22 entering the vein. In some embodiments, the alert patch 114 may provide the third alert in response to the catheter 22 being fed further into the vein. In some embodiments, the alert patch 114 may be configured to provide the fourth alert in response to the catheter 22 being fully inserted into the vein, which may signal the introducer needle 30 can be removed from the catheter 22. In some embodiments, each of the first, second, third, and fourth alerts may include a different light, which may be activated, blink, stop blinking, change color, etc.

In some embodiments, the alert patch 114 may facilitate easy visualization of the phase of insertion of the catheter assembly while the clinician is physically performing the insertion of the catheter assembly. In some embodiments, one or more of the alerts may change or cease in response to one or more of the following: the introducer needle 30 no longer being present in the vein, the catheter 22 no longer be present in the vein, or the catheter 22 no longer being fully inserted within the vein.

Again, it is understood that the embodiments of the present application may be combined. As an example, the embodiments of FIGS. 8A-8D may include one or more holes 66 (illustrated, for example, in FIGS. 2B, 4-5, and 7) in addition to or as an alternative to one or more channels 90. As another example, the embodiments of FIGS. 9A-9C may include one or more holes 66 (illustrated, for example, in FIGS. 2B, 4-5, and 7) in addition to or as an alternative to one or more channels 90.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a catheter adapter, comprising a distal end and a proximal end;
   a catheter, comprising a distal end, a proximal end, a catheter lumen extending through the distal end of the catheter and the proximal end of the catheter, and an inner surface forming the catheter lumen, wherein the catheter extends distally from the distal end of the catheter adapter, wherein the distal end of the catheter comprises a hole;
   an introducer needle extending through the catheter, wherein the introducer needle comprises a distal end, a proximal end, an introducer needle lumen extending through the distal end of the introducer needle and the proximal end of the introducer needle, and an inner surface forming the introducer needle lumen, wherein the distal end comprises a sharp distal tip;
   a gap disposed between an outer surface of the introducer needle and the inner surface of the catheter and within the catheter lumen, wherein the gap is in fluid communication with the hole such that in response to the hole being inserted into a vein, blood may flow through the hole and into the gap; and
   a bio-impedance sensor, wherein the bio-impedance sensor comprises a first electrode and a second electrode, wherein the first electrode is embedded in the inner surface of the introducer needle at the distal end of the introducer needle or an outer surface of the catheter at the distal end of the catheter within the gap, wherein the second electrode is configured to be secured to skin of a patient.

2. The catheter system of claim 1, wherein the gap is annular.

3. The catheter system of claim 1, further comprising a plurality of other sensors, wherein the plurality of other sensors comprise bio-impedance sensors, wherein the bio-impedance sensor and the plurality of other sensors are aligned with a bevel of the introducer needle.

4. A catheter system, comprising:
a catheter adapter, comprising a distal end and a proximal end;
a catheter, comprising a distal end, a proximal end, a catheter lumen extending through the distal end and the proximal end, and an inner surface forming the catheter lumen, wherein the catheter extends distally from the distal end of the catheter adapter, wherein the distal end of the catheter comprises a distal opening;
an introducer needle extending through the distal opening, wherein the introducer needle comprises a sharp distal tip;
a first position indicator configured to indicate the introducer needle is inserted into a vein, wherein the first position indicator comprises a notch disposed within the introducer needle and proximate a gap disposed between an outer surface of the introducer needle and an inner surface of the catheter, wherein the first position indicator further comprises an absorbent material disposed within the notch; and
a second position indicator configured to indicate the catheter is inserted into the vein.

5. The catheter system of claim 4, wherein the second position indicator is configured to indicate the catheter is inserted into the vein a first amount, further comprising a third position indicator configured to indicate the catheter is inserted within the vein a second amount.

6. The catheter system of claim 4, wherein the second position indicator comprises a marking disposed on an outer surface of the catheter.

7. The catheter system of claim 6, further comprising a third position indicator, wherein the third position indicator comprises:

a lumen disposed within a wall of the catheter and an aperture at a distal end of the lumen, wherein the aperture extends through the wall;
a groove within the outer surface of the introducer needle and a hole at a distal end of the groove extending through the wall of the catheter;
a sensor embedded in the outer surface of the catheter; or
a marking disposed on an outer surface of the catheter.

8. A catheter system, comprising:
a catheter adapter, comprising a distal end and a proximal end;
a catheter, comprising a distal end, a proximal end, a catheter lumen extending through the distal end of the catheter and the proximal end of the catheter, and an inner surface forming the catheter lumen, wherein the catheter extends distally from the distal end of the catheter adapter, wherein the distal end of the catheter comprises a first hole and a second hole proximal to the first hole;
an introducer needle extending through the catheter, wherein the introducer needle comprises a sharp distal tip, a first groove, and a second groove, wherein a distal end of the first groove is proximate the first hole, wherein a distal end of the second groove is proximate the second hole; and
a gap disposed between an outer surface of the introducer needle and the inner surface of the catheter and within the catheter lumen, wherein the gap is in fluid communication with the first hole such that in response to the first hole being inserted into a vein, blood may flow through the first hole and into the gap, wherein the gap is disposed within the first groove.

* * * * *